(12) United States Patent
Love et al.

(10) Patent No.: US 12,397,841 B2
(45) Date of Patent: Aug. 26, 2025

(54) CART STABILIZATION DEVICES, SYSTEMS, AND METHODS

(71) Applicant: NuVasive, Inc., San Diego, CA (US)

(72) Inventors: John Love, San Diego, CA (US); Todd Baxendale, Broomfield, CO (US)

(73) Assignee: Nuvasive Inc., San Diego, CA (US)

( * ) Notice: Subject to any disclaimer, the term of this patent is extended or adjusted under 35 U.S.C. 154(b) by 0 days.

(21) Appl. No.: 18/762,190

(22) Filed: Jul. 2, 2024

(65) Prior Publication Data
US 2024/0359721 A1 Oct. 31, 2024

Related U.S. Application Data

(63) Continuation of application No. 17/461,342, filed on Aug. 30, 2021, now Pat. No. 12,049,248.

(51) Int. Cl.
*A61B 34/20* (2016.01)
*A61B 50/13* (2016.01)
*B62B 5/04* (2006.01)

(52) U.S. Cl.
CPC .............. *B62B 5/049* (2013.01); *A61B 50/13* (2016.02); *B62B 5/0404* (2013.01); *B62B 2301/044* (2013.01)

(58) Field of Classification Search
CPC . B62B 5/049; B62B 5/0404; B62B 2301/044; A61B 50/13
USPC .................................................. 188/5–7, 19
See application file for complete search history.

(56) References Cited

U.S. PATENT DOCUMENTS

| | | | | |
|---|---|---|---|---|
| 1,200,022 | A * | 10/1916 | Price | B60G 11/36 267/168 |
| 2,922,494 | A * | 1/1960 | Clark, Jr. | B60B 33/0089 188/5 |
| 4,833,972 | A * | 5/1989 | Bohusch | A61G 13/10 91/465 |
| 6,336,524 | B1 * | 1/2002 | Van Loon | B62B 5/0485 188/19 |
| 12,049,248 | B2 * | 7/2024 | Love | A61B 50/13 |
| 2011/0303497 | A1 * | 12/2011 | Gaffney | B60T 7/042 188/106 P |
| 2015/0096815 | A1 * | 4/2015 | Ottenweller | A61G 7/0528 180/19.1 |

(Continued)

FOREIGN PATENT DOCUMENTS

| | | |
|---|---|---|
| CN | 110722927 A | 1/2020 |
| KR | 20180007882 A | 1/2018 |

(Continued)

*Primary Examiner* — Christopher P Schwartz

(57) ABSTRACT

Devices, assemblies, systems, and methods are disclosed for stabilizing a cart. An example cart is a surgical cart having a robotic arm thereon. A stabilizer system may be part of or used with the cart to stabilize the cart at a location. The stabilizer system may include a stabilizer and an actuator. The stabilizer may have a foot and a biaser configured to bias the foot to a retracted position and contribute to an amount of force applied to a floor supporting the cart when the foot is in a deployed position. The actuator acts on the stabilizer to overcome a bias force biasing the stabilizer to the retracted position and cause feet of the stabilizer to contact the floor. Once the feet of the stabilizer contact the floor, a spring of the biaser causes the foot to apply a predetermined force amount to the floor.

12 Claims, 8 Drawing Sheets

(56) References Cited

U.S. PATENT DOCUMENTS

2018/0304113 A1  10/2018  Goldish et al.
2022/0153364 A1* 5/2022  Nahum .................. B62B 5/049

FOREIGN PATENT DOCUMENTS

WO    2016145044  A1    9/2016
WO    2018154750  A1    8/2018

* cited by examiner

CART STABILIZATION DEVICES, SYSTEMS, AND METHODS

CROSS REFERENCE TO RELATED APPLICATIONS

The present application is a continuation of U.S. patent application Ser. No. 17/461,342 (published as U.S. 2023-0062720), filed Aug. 30, 2021, the entirety of which is hereby incorporated by reference.

BACKGROUND

A wide variety of surgical devices and systems have been developed for medical use, for example, surgical use. Some of these devices and systems include carts for use in surgical procedures, among other devices and systems. These devices and systems are manufactured by any one of a variety of different manufacturing methods and may be used according to any one of a variety of methods. Of the known surgical devices, systems, and methods, each has certain advantages and disadvantages. There is an ongoing need to provide alternative surgical devices and systems, as well as alternative methods for manufacturing and using the surgical devices and systems.

BRIEF SUMMARY

This disclosure provides design, material, manufacturing method, and use alternatives for devices, systems, assemblies used in medical procedures. An example assembly includes a surgical cart having locking caster wheels configured to contact a floor, a stabilizer, and an actuator configured to drive the stabilizer toward a deployed position. The stabilizer may include a foot configured to resist movement of the surgical cart when the foot is in a deployed position contacting the floor, and a biaser configured to bias the foot in a retracted position and contribute to a predetermined amount of force applied to the floor when the foot is in the deployed position. Actuation of the actuator causes the stabilizer to adjust to the deployed position and apply the predetermined amount of force to the floor.

Alternatively or additionally to any of the embodiments in this section, the biaser comprises a first spring biasing the stabilizer to the retracted position, and a second spring biasing the stabilizer to the deployed position.

Alternatively or additionally to any of the embodiments in this section, the biaser comprises a housing, wherein the first spring extends along an exterior of the housing and the second spring extends along an interior of the housing.

Alternatively or additionally to any of the embodiments in this section, the surgical cart comprises a surgical cart base, and the biaser comprises a biaser housing, and a spring configured to act on the surgical cart base and the biaser housing to bias the stabilizer in the retracted position.

Alternatively or additionally to any of the embodiments in this section, the stabilizer comprises a rod, a plate fixed relative to the rod, and a foot connected to the rod and configured to contact the floor when the stabilizer is in the deployed position, wherein the biaser comprises a biaser housing, and a spring extending within the biaser housing, and wherein the spring is configured to act on the biaser housing and the plate to contribute to the predetermined amount of force applied to the floor when the stabilizer is in the deployed position.

Alternatively or additionally to any of the embodiments in this section, the assembly further comprises a force sensor configured to directly or indirectly measure an amount of force applied to the floor when the stabilizer is in the deployed position.

Alternatively or additionally to any of the embodiments in this section, the predetermined amount of force applied to the floor when the stabilizer is in the deployed position is less than a force required to lift the surgical cart off of the floor.

Alternatively or additionally to any of the embodiments in this section, the predetermined amount of force applied to the floor when the stabilizer is in the deployed position is within a range of 80 pounds of force to 100 pounds of force.

Alternatively or additionally to any of the embodiments in this section, the stabilizer is a first stabilizer, the assembly further comprises a second stabilizer spaced from the first stabilizer, and the actuator is configured to simultaneously drive the first stabilizer and the second stabilizer toward the deployed position.

Alternatively or additionally to any of the embodiments in this section, the assembly further comprises a mechanical release, wherein the mechanical release is configured to mechanically disengage the actuator and cause the stabilizer to move from the deployed position to the retracted position.

Alternatively or additionally to any of the embodiments in this section, the actuator is configured to drive the stabilizer between the retracted position and the deployed position without regard to an amount of force being applied to the floor by the stabilizer.

A further example may include a system comprising a first stabilizer and a second stabilizer for stabilizing a surgical cart on wheels, a force applicator extending between the first stabilizer and the second stabilizer, and a linear actuator configured to pull down on the force applicator to cause the first and second stabilizers to move from a retracted position to a deployed position.

Alternatively or additionally to any of the embodiments in this section, the force applicator includes a first end interacting with the first stabilizer, a second end interacting with the second stabilizer, and a portion between the first end and the second end that is coupled to the linear actuator.

Alternatively or additionally to any of the embodiments in this section, the force applicator extends between the linear actuator, the first stabilizer, and the second stabilizer, and wherein the linear actuator is arranged to pull the force applicator toward a floor supporting the surgical cart to cause the first and second stabilizers to move toward the deployed position.

Alternatively or additionally to any of the embodiments in this section, each of the first and second stabilizers comprise a foot configured to contact a floor to support the surgical cart when the stabilizer is in the deployed position, and a biaser configured to bias the stabilizer in the retracted position and contribute to an amount of force the foot applies to the floor in the deployed position.

Alternatively or additionally to any of the embodiments in this section, the foot of each stabilizer is configured to initially translate with the force applicator and a biaser housing of the biaser when the stabilizer is moving from the retracted position to the deployed position and once the foot of each stabilizer contacts the floor, translate relative to the force applicator and the biaser housing.

Alternatively or additionally to any of the embodiments in this section, wherein the linear actuator is configured to adjust between a first predetermined position associated with the retracted position and a second predetermined position associated with the deployed position irrespective of the amount of force the feet of the first and second stabilizers apply to the floor in the deployed position.

Alternatively or additionally to any of the embodiments in this section, the system may further comprise a force sensor in communication with the linear actuator, the force sensor is configured to sense a force indicative of a force the first stabilizer and the second stabilizer apply to a floor contacting the first stabilizer and the second stabilizer when the first stabilizer and the second stabilizer are in the deployed position, and a controller configured to classify the deployment of the first stabilizer and the second stabilizer as being successful or unsuccessful based on an amount of force detected by the force sensor.

A further example may include an assembly comprising a surgical cart for supporting a robotic arm and having locking casters, a first stabilizer supported by the surgical cart and having a first biaser and a first foot, a second stabilizer supported by the surgical cart and having a second biaser and a second foot, an actuator configured to adjust between a first position and a second position, and a force applicator configured to apply a force from the actuator to the first stabilizer and the second stabilizer. An adjustment of the actuator from the first position to the second position may move the first stabilizer and the second stabilizer from a retracted position to a deployed position. Each foot is configured to initially translate with the force applicator when the first stabilizer and the second stabilizer are moving from the retracted position to the deployed position and then, translate relative to the force applicator when the first stabilizer and the second stabilizer are moving from the retracted position to the deployed position. The first stabilizer and the second stabilizer are configured to stabilize the surgical cart when the first stabilizer and the second stabilizer are in the deployed position.

Alternatively or additionally to any of the embodiments in this section, the actuator is a linear actuator configured to linearly adjust between the first position and the second position without regard to an amount of force being applied by the first stabilizer and the second stabilizer to a floor supporting the surgical cart.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
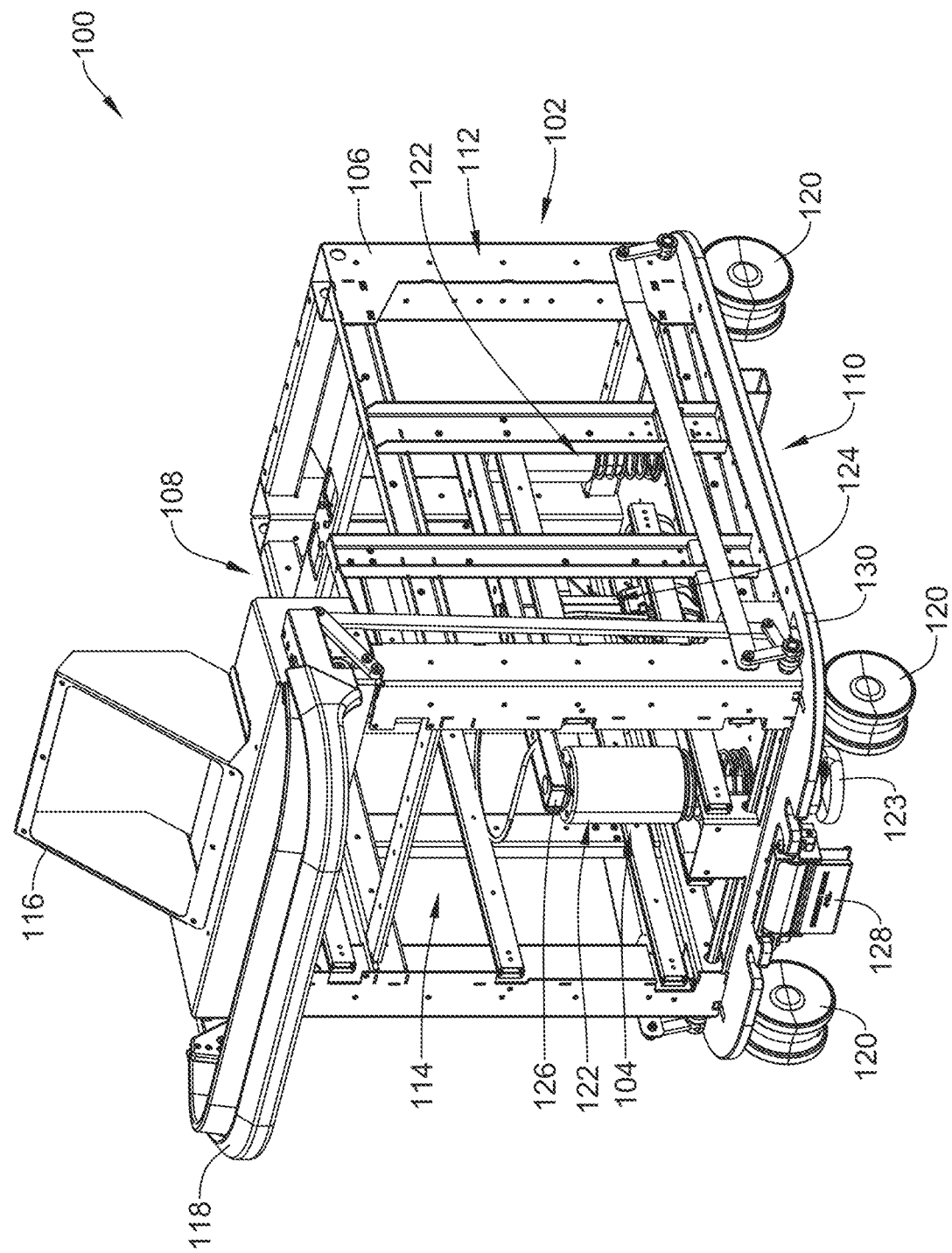
FIG. 1 is a schematic perspective view of an illustrative surgical cart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

Carts may be used in or to facilitate surgical procedures. In some cases, carts may include one or more robots or robotic components for use in a surgical procedure. Such carts (e.g., robot carts or other suitable carts) often need to alternate between highly mobile states for transport and highly immobile states when the carts or components on the carts are being used in a surgical procedure or are otherwise being used. Often, locking casters are used to support the cart, which facilitate moving the cart in the highly mobile state, but can be insufficient, at least on their own, to fully stabilize the cart for use in surgical procedures in the highly immobile state.

An assembly may include a cart and a stabilization system for use with the cart. The stabilization system may include feet that are deployed to apply a force to a surface or floor on which the cart is supported without lifting the cart off the surface or floor. In operation, a cart including the stabilization system and locking caster wheels may be moved to a desired location and once at the desired location, the locking caster wheels may be locked and feet of the stabilization system may deploy from beneath the cart or other suitable location.

In one example implementation of the stabilization system, the stabilization system may include a first and second stabilizer each having a foot for contacting a floor, a crossbar (e.g., a force applicator), and an actuator. In operation, the actuator is activated in a first direction and pulls down on the crossbar acting on the stabilizers, which results in the stabilizers overcoming a bias force such that the feet are extended to the ground surface and apply force to the floor or another surface to stabilize the cart. To withdraw the feet from the floor, the actuator is released or activated in a second direction opposite of the first direction such that a bias force of the stabilizers overcomes a force, if any, acting thereon by the crossbar and causes the feet to withdraw from the surface.

The amount of force applied to the surface by the feet may be any suitable amount of force that is able to stabilize the cart. The force may, but need not, be sufficient lift the cart (e.g., casters or other suitable portions of the cart) off of the surface on which the cart is supported. In one example, an amount of forced applied to a surface supporting the cart by the stabilizers may be in the range of about eighty pounds of force to about one-hundred pounds of force. Other suitable force amounts are contemplated.

Turning to the Figures, FIG. 1 depicts a schematic perspective view of an illustrative cart assembly 100. The cart assembly 100 may include a cart 102 and a stabilizing system 104, among other suitable components.

The cart 102 may be a cart that is configured for use in surgical procedures. In one example, the cart 102 may include or may be configured to receive a surgical robot (e.g., robotic arms, etc.) or other suitable teleoperated surgical systems.

The cart 102 may include a frame structure 106. The frame structure 106 may have any suitable design or configuration that facilitates supporting one or more items for use in a surgical procedure, such as one or more computer systems, cameras, lights, instruments, surgical robots, suitable teleoperated surgical systems, related components, or combinations thereof. In some cases, the frame structure 106 may include or otherwise be supported by a base 130 (e.g., a surgical cart base).

As depicted in FIG. 1, the frame structure 106 may have or define a top 108, a bottom 110, and one or more sides 112 of the cart, where the one or more sides 112 may extend entirely or at least partially between the top 108 and the bottom 110. In some cases, the top 108, the bottom 110, and the one or more sides 112 may define a central space 114 in which one or more components of or used with the cart assembly 100 may be located. The frame structure 106 may include struts, frame bars, supports, or other suitable components to support defining the top 108, the bottom 110, and the sides 112, along with components connected thereto or supported thereby. Although not depicted, one or more of the top 108, the bottom 110, and the sides 112 may include or have thereon a cover or other suitable solid or partially solid surface.

The top 108 of the cart 102 may be configured to support one or more surgical system components or other components. Although not required, the top 108 may have one or more components configured to facilitate securing the surgical system components or other components to the cart 102. An example surgical system component secured to the cart 102 (e.g., secured to the top 108 of the cart 102 or other suitable location) may be a robotic surgical arm, thought other components are contemplated.

The bottom 110 of the cart 102 may be configured to support one or more components located at least partially within the central space 114. In one example, as depicted in FIG. 1, the stabilizer system 104 may be supported by the bottom 110 of the cart 102. Such a configuration is not required, and the stabilizer system 104 may be supported by one or more other portions of the cart 102.

The frame structure 106 may support or define other features of the cart 102. As depicted in FIG. 1, the frame structure 106 may include one or more monitor supports 116 and one or more handles 118, among other suitable features. The monitor support 116 may be configured to receive a display or control system configured to be used with (e.g., to facilitate control of) components supported by the cart 102 or surgical components. In some cases, the handle 118 may be configured as a rigid handle or the handle 118 may have an adjustable portion that may be adjusted to lock or unlock wheels of the cart 102, but this is not required. Although the monitor support 116 and the handle 118 are described herein as being part of the frame structure 106, the monitor support 116 or the handle 118 may be separate from the frame structure 106 and supported by the frame structure 106.

The cart 102 may include one or more wheels 120 that may be configured to facilitate supporting the cart 102 on a surface or floor and facilitate movement of the cart 102 on or along the surface or floor. In one example, the cart may include four wheels 120 (though, only three are visible in FIG. 1).

The wheels 120 may be of any suitable type or suitable combination of types configured to support the cart 102 and facilitate transporting the cart along a floor or other suitable surface. Example types of wheels 120 include, but are not limited to, rigid caster wheels, swivel caster wheels, locking wheels, locking caster wheels, kingpinless caster wheels, omnidirectional wheels, etc. In one example, the cart 102 may include one or more wheels 120 that are of the locking caster type.

When cart 102 includes one or more locking wheels 120 (e.g., locking caster wheels, etc.), wheels 120 may be configured to manually lock or unlock. In one example, the wheels 120 may be manually locked at each individual wheel 120. In another example, one or more of the wheels 120 may be manually locked or unlocked by a user actuating a mechanical locking system that locks-in-place or unlocks one or more of the wheels 120.

Alternatively or additionally, the wheels 120 may be configured to lock or unlock in an automated manner in response to an action by a user or a positioning of a cart at a location in a room. In one example, the wheels 120 may be locked-in-place or unlocked in response to a user selecting, or a control system receiving a selection of, a button or other suitable actuator that initiates an electromechanical system to lock or unlock one or more of the wheels 120. In another example, the wheels 120 may be locked-in-place or unlocked in response to a positioning system in a room (e.g., surgery room or other suitable room) identifying the cart 102 is at a desired or predetermined location within the room or with respect to a feature in the room and initiating an electromechanical system to lock or unlock one or more of the wheels in response to identifying the position of the cart 102.

As discussed above, the cart assembly 100 may include the stabilizer system 104. Among other features, and as discussed in greater detail below, the stabilizer system 104 may include one or more stabilizers 122 having a foot 123 or other suitable feature for engaging a floor or other surface to facilitate stabilizing the cart 102, one or more actuators 124 configured to drive the stabilizer(s) 122 toward a deployed position or a retracted position, and one or more force applicator 126 (e.g., a crossbar or other suitable force applicator) coupling the one or more actuators 124 and the one or more stabilizers 122. In one example, the stabilizer system 104 may include two stabilizers 122.

In operation, when the one or more actuators 124 are actuated, the actuator(s) may drive the stabilizer(s) 122 from an undeployed state (e.g., a retracted or resting position) to a fully-deployed state or at least partially deployed state causing the feet 123 to move toward or to a floor or other suitable surface. When two or more stabilizers 122 are utilized with the force applicator 126, actuating the actuator 124 may simultaneously drive the stabilizers 122 (e.g., via the force applicator 126) toward the deployed position. Simultaneously drive of the stabilizers 122, however, is not required and the configuration of the stabilizers 122, the actuator(s) 124, and the force applicator(s) 126 may be alternatively or additionally configured such that one or more of the stabilizers 122 are actuated separate or independent from one or more of the stabilizers 122. When in a fully deployed state such that the feet 123 are in contact with the floor or other suitable surface and applying a force thereto, the feet 123 and the stabilizer(s) 122 may resist movement of, or otherwise stabilize, the surgical cart 102.

The actuator(s) 124 may be manually actuated or actuated in an automated manner. In some cases, actuation of the actuator 124 may be performed automatically in response to or at the time of locking the wheels 120, but this is not required.

The cart 102 may include an emergency release 128 (e.g., a mechanical release). In some cases, the emergency release 128 may be coupled to the locks or locking system of the wheels 120, part of or coupled to the stabilizer system 104, or coupled to both of the locks or locking system of the wheels 120 and the stabilizer system 104. When the emergency release 128 is coupled to the locks or locking system of the wheels 120 and the stabilizer system 104 and the emergency release 128 is actuated, the locks or locking system of the wheels 120 may cause the wheels 120 to be in an unlocked state and the stabilizer system 104 may cause the stabilizers 122 to move the feet 123 to a fully or at least partially withdrawn or retracted position such that the cart 102 may be moved along a floor or other suitable surface.

Figure 2:
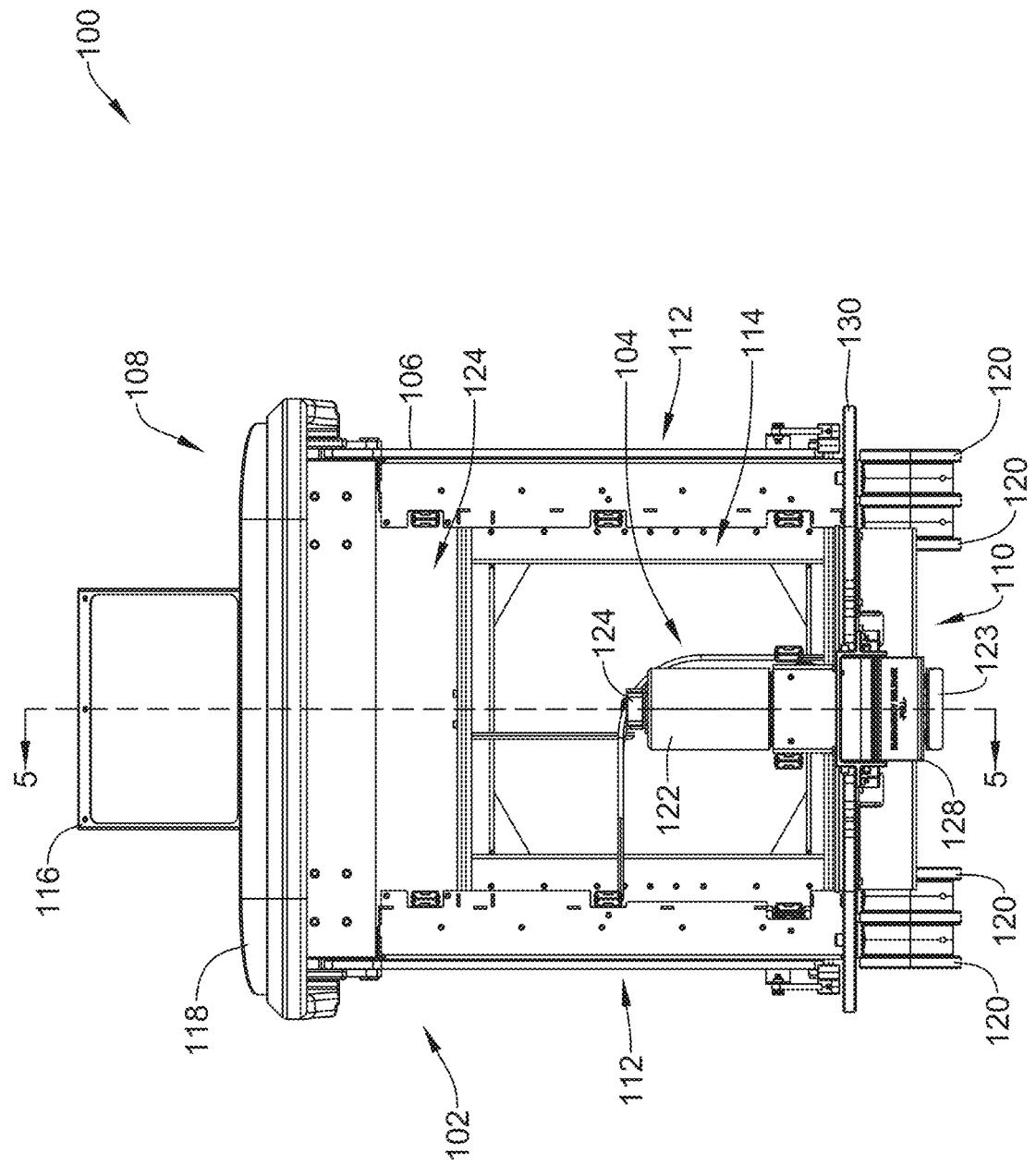
FIG. 2 is a schematic end view of the illustrative surgical cart of FIG. 1.

FIG. 2 depicts a schematic end view of the cart assembly 100. FIGS. 5-8 depict cross-sectional views of the cart assembly 100 taken along line 5-5 in FIG. 2.

The schematic end view shown in FIG. 2 depicts an end of the cart 102 at which the monitor support 116 and the handle 118 are located. As can be seen in FIG. 2, the cart assembly 100 may include four wheels 120, where the front wheels 120 may be slightly offset (e.g., inward) from the back wheels 120, but this is not required and the wheels 120 may be offset in a different manner or not offset at all. Further, the stabilizer system 104 may be centrally located within the cart 102 between opposite sides 112. The stabilizer system 104 centrally located in the cart 102 may facilitate providing well-balanced stabilization of the cart 102 when the stabilizers 122 are in a deployed position. Although the stabilizer system 104 is centrally located within the central space 114 in the cart assembly 100 configuration depicted in FIG. 2, the stabilizer system 104 may be located elsewhere with respect to cart 102.

Figure 3:
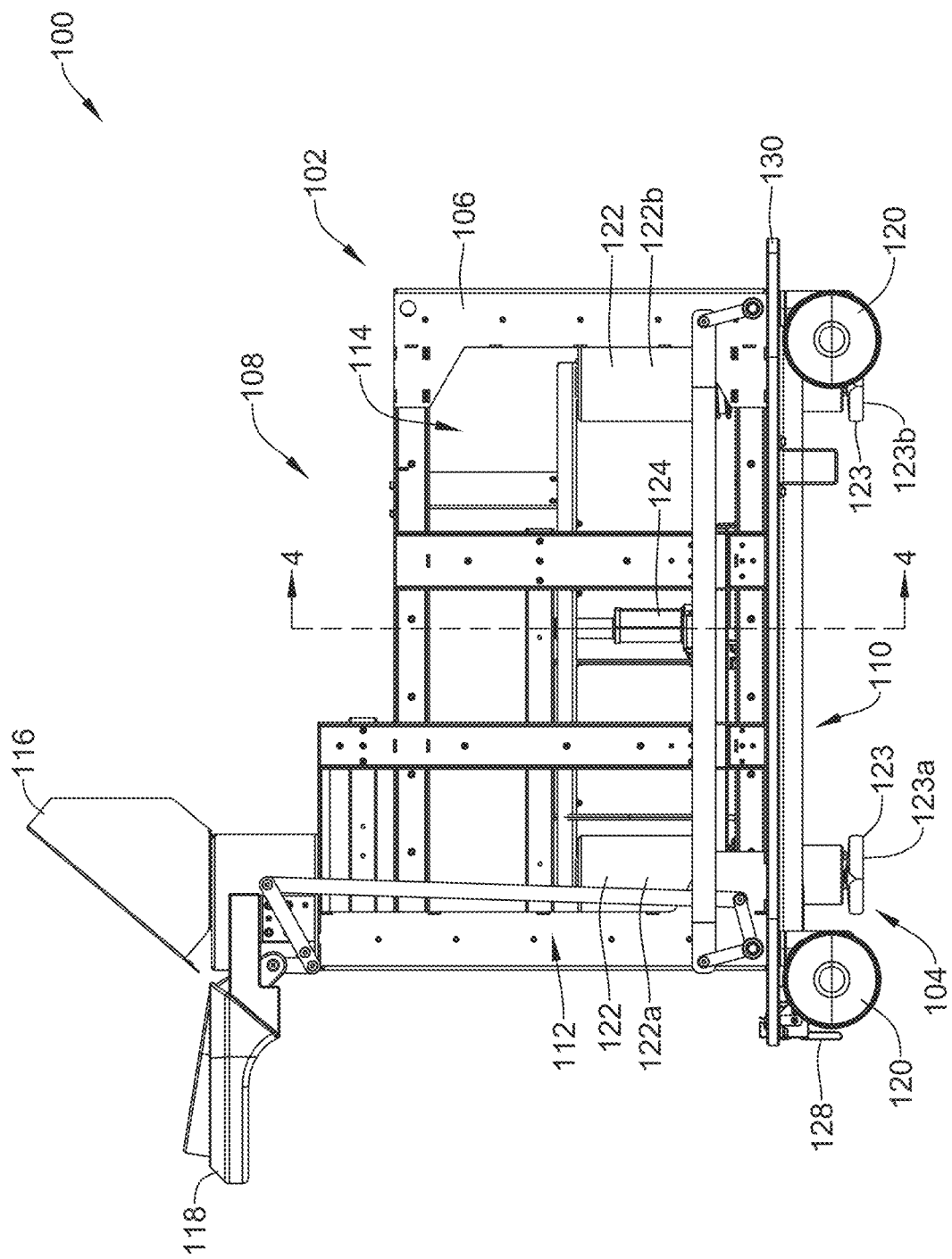
FIG. 3 is a schematic side view of the illustrative surgical cart of FIG. 1.
Figure 4:
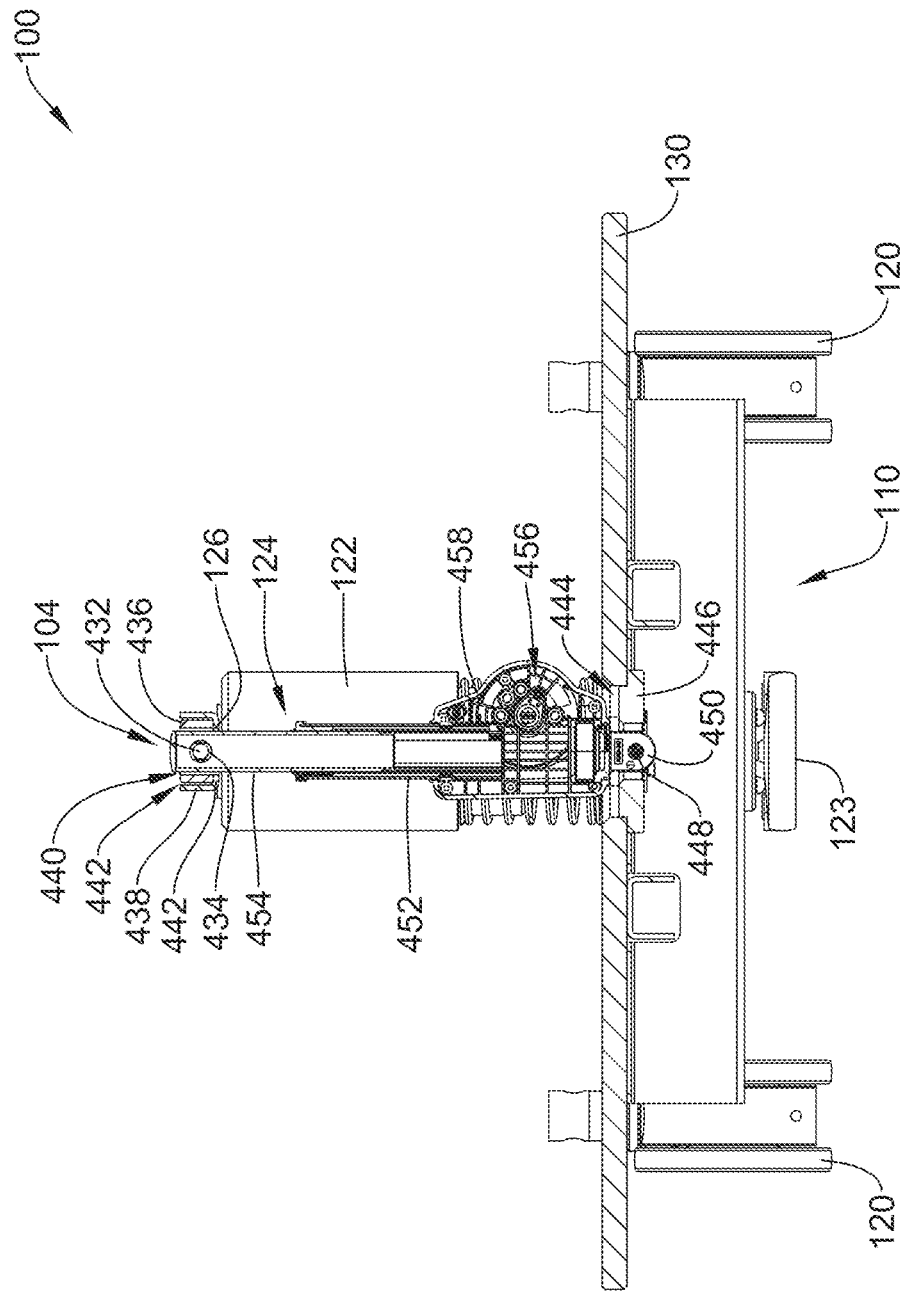
FIG. 4 is a schematic cross-sectional view of an illustrative cart base and stabilization system of the surgical cart of FIG. 1, taken along line 4-4 in FIG. 3.

FIG. 3 depicts a schematic side view of the cart assembly 100. FIG. 4 depicts a cross-sectional view of the cart assembly 100 taken along line 4-4 in FIG. 3.

As can be seen in FIG. 3 due to only depicting a front wheel 120 and a back wheel 120, the front wheels 120 are axially aligned and the back wheels 120 are axially aligned. Further, the stabilizer system 104 may include a first stabilizer 122a with an associated first foot 123a and a second stabilizer 122b with an associated second foot 123b. As depicted, the first stabilizer 122a may be located closer to a first end (e.g., a back end) of the cart 102 and the second stabilizer 122b may be located closer to a second end (e.g., a front end) of the cart 102. The stabilizers 122 may be spaced from the ends of the cart 102 as desired to facilitate stabilizing the cart when in use.

FIG. 4 depicts a schematic cross-sectional view of the cart assembly 100. The cross-sectional view of the cart assembly 100 is taken along line 4-4 in FIG. 3, showing the actuator 124 coupled to the force applicator 126 and the base 130 of the cart 102 with the frame structure 106 removed.

As discussed above, the force applicator 126 may be coupled to the actuator 124 and the stabilizer(s) 122 such that the actuator 124 may act on the force applicator 126 to cause the force applicator 126 to apply a force to the stabilizer(s) 122. The actuator 124 may be coupled to the force applicator 126 in any suitable manner that facilitates the actuator 124 acting on the force applicator 126. Example couplings between the force applicator 126 and the actuator 124 may include, but are not limited to, a pin connection, a threaded connection, a luer lock connection, a bayonet connection, a friction fit connection, a snap connection, other suitable couplings, or combinations thereof.

In one example configuration of the coupling between the force applicator 126 and the actuator 124, as depicted in FIG. 4, the actuator 124 may be coupled to the force applicator 126 with a pin 432 to create a pin connection. In the example, the pin 432 may be inserted into an opening 434 extending through the actuator 124 and the actuator 124 with the pin 432 may be inserted into the force applicator 126. In such a configuration, when the actuator 124 is adjusted or otherwise actuated, the pin may act on the force applicator 126 to cause the force applicator 126 to change position. The pin 432 may be part of the actuator 124 or a separate component used with the actuator 124.

The force applicator 126 may have any suitable configuration. Example configurations of the force applicator 126 may include a single elongated component or bar, a multi-piece component or bar, or one or more other suitable configuration. In one example, as depicted in FIG. 4, the force applicator may include a first elongated component 436 and a second elongated component 438. Although not required, the first elongated component 436 may have a bar configuration having an opening 440 for receiving the actuator 124 and the pin 432. The second elongated component 438 may have a U-bracket configuration that is configured to receive and couple to (e.g., via any suitable connectors) the first elongated component 436, but this is not required and other configurations are contemplated. Further, the second elongated component 438 may have an opening 442 configured to receive the actuator 124.

The force applicator 126 may be formed from any suitable material configured to withstand forces applied to it in use with the actuator 124 and the stabilizer(s) 122. Example materials include, but are not limited to, metals, polymers, stainless steel, sheet metal, combination of metals and polymers, etc.

The actuator 124 may be coupled to the base 130 in any suitable manner. In the example depicted in FIG. 4, the actuator 124 may extend through an opening 444 in the base 130 and may be coupled to a connector plate 446 that is secured to the base 130. In the example depicted in FIG. 4, a pin 448 may extend through a clevis 450 to connect the actuator 124 to the connector plate 446. Other suitable configurations are contemplated. Any suitable types of couplings or connectors may be utilized to couple or connect the actuator 124, the base 130, and the connector plate 446 including, but not limited to, screws, bolts, nuts, washers, spacers, pins, etc.

The actuator 124 may be any suitable type of actuator configured to apply a pulling or pushing force on the force applicator 126 and in-turn the stabilizer(s) 122. Example types of actuators include, but are not limited to, linear actuators, rotary actuators, hydraulic actuators, pneumatic actuators, electric actuators, thermal magnetic actuators, mechanical actuators, supercoiled polymer actuators, or other suitable actuators and combinations of actuator types. In one example, the actuator 124 may be an electric motor driven linear actuator, but this is not required.

The electric motor linear actuator 124 depicted in FIG. 4 may have a variety of components. As depicted, the actuator 124 may include an outer tube 452 (e.g., a cover tube), an inner tube 454 (e.g., an extension tube, drive tube, translating tube, etc.), an electric motor 456, and a motor housing 458. The actuator 124 may include other components not depicted that include, but are not limited to, a spindle or lead screw, a safety stop located on the end of the spindle to prevent over extension of the inner tube, a wiper between the outer tube 452 and the inner tube 454, a drive nut attached to the inner tube 454 and travels along the spindle, limit switch to control the fully extended and retracted inner tube position by cutting current to the motor, a gear, etc.

Figure 5:
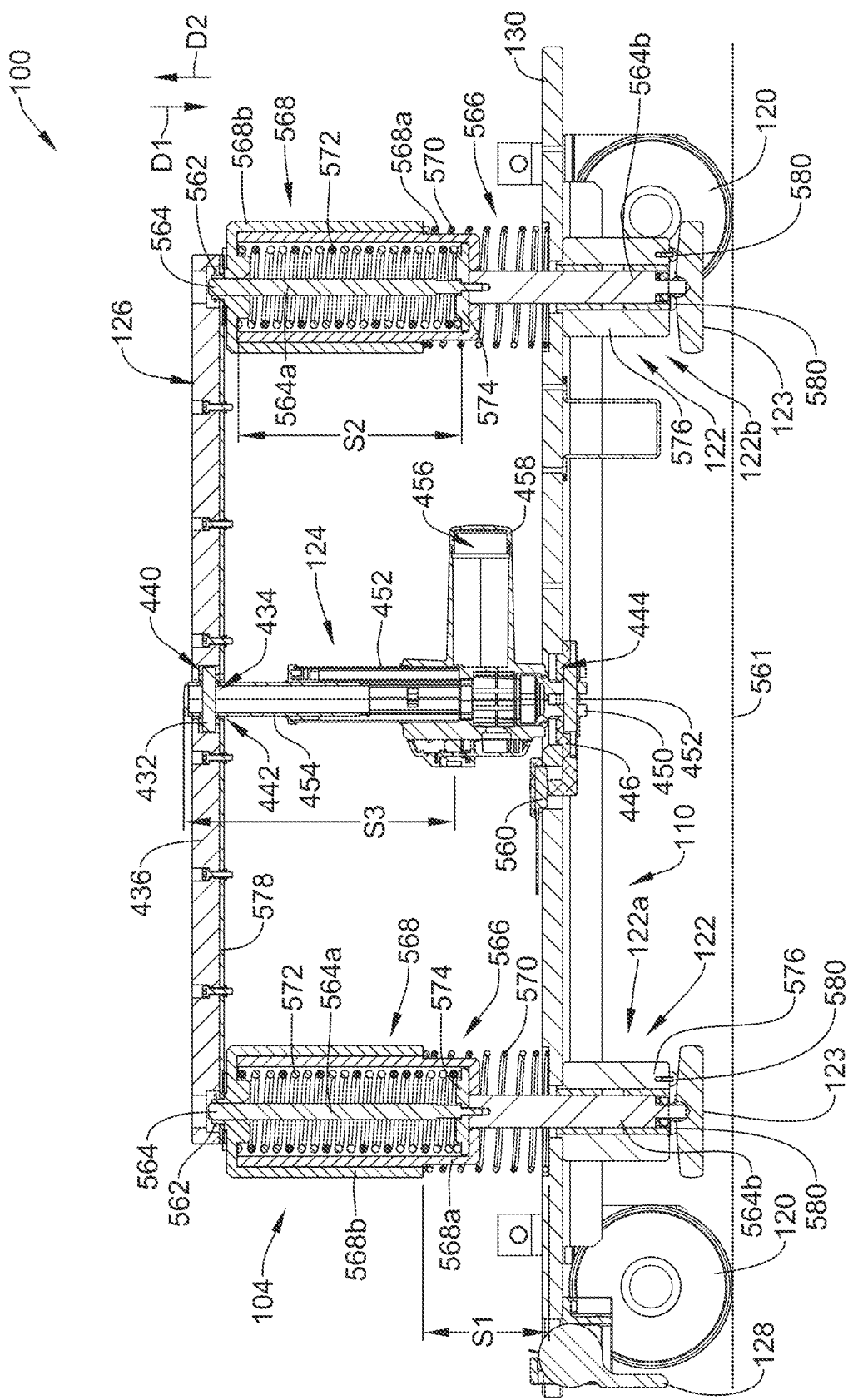
FIG. 5 is a schematic cross-sectional view of the illustrative cart base and stabilization system of the surgical cart of FIG. 1, taken along line 5-5 in FIG. 2.

FIG. 5 depicts a schematic cross-sectional view of the cart assembly 100. The cross-sectional view of the cart assembly 100 taken along line 5-5 in FIG. 2, shows, among other features, the force applicator 126 coupled to the actuator 124 and the stabilizers 122 (e.g., a first stabilizer 122a and a second stabilizer 122b).

The stabilization system 104 may include one or more pressure or force sensors 560 for determining an amount of force the stabilizers 122 are applying to a floor or surface 561 supporting the cart 102. The force sensor(s) 560 may be configured to directly, indirectly, or both indirectly and directly measure or sense the amount of force applied to or indicative of the amount of force applied to the floor or surface 561 when the stabilizer(s) 122 are in a deployed position. A sensed or measured force may be utilized for any suitable purpose including, but not limited to, as a check on the actuator 124 to ensure the actuator 124 is operating at specifications. If it is determined that the actuator 124 is not operating at specifications, data from the force sensor 560 may be utilized to determine the health of the actuator 124 and actions to take for addressing the actuator 124 not operating at specifications. Additionally or alternatively, the output of the force sensor(s) 560 may be utilized (e.g., by a controller of the cart assembly 100, or other suitable controller, receiving an output signal directly or indirectly from the force sensor 560) to classify a deployment of the stabilizer(s) 122 as being successful or unsuccessful based on an amount of force detected by the force sensor 560. In response to detecting an unsuccessfully deployment, the controller may provide a notification, take a corrective action, make a second deployment attempt, or take other suitable action, but this is not required.

The force sensors 560 may be located at any suitable location(s) along the stabilizer system 104 at which an amount of force applied to or indicative of the amount of force applied to the floor or surface 561 when the stabilizer(s) 122 are in the deployed position may be measured or sensed. In one example when the force sensor 560 is configured to directly measure the force applied to the floor or surface 561, the force sensor 560 may be located in the foot 123 of the stabilizer 122 such that one portion of the force sensor 560 is configured to contact the floor or surface 561 and another portion of the force sensor 560 is configured to contact the stabilizer 122. In another example, when the force sensor 560 is configured to indirectly measure the force applied to the floor or surface, the force sensor 560 may be spaced away from the foot 123 that is applying force to the floor or surface 561, or otherwise configured so as not to be in direct contact with the floor or surface 561.

In some cases, the force sensor 560 may be secured to the base 130 of the cart 102 and the connector plate 446 to which the actuator 124 is coupled. In such a configuration, when the actuator 124 is acting on the force applicator 126 and the stabilizer(s) 122 in a first direction represented by arrow D1, the actuator 124 applies a force to the connector plate 446, which in turn applies a force between the force sensor 560 and the base 130. The force between the force sensor 560 and the base 130 is an indirect measure of the amount of force applied to the floor or other surface when the stabilizer(s) 122 are in the deployed position. Other configurations are contemplated.

The pressure or force sensors 560 may be of any suitable type. Example pressure or force sensor types include, but are not limited to, load cells, strain gages, for sensing resistors, optical force sensors, ultrasonic force sensors, pneumatic load cells, hydraulic load cells, piezoelectric crystal load cells, inductive load cells, capacitive load cells, magnetoresistive load cells, strain gage load cells, other types, or combinations thereof.

When the stabilizer system 104 includes two stabilizers 122, the actuator 124, and the force applicator 126, the two stabilizers 122 may be located at any desired location with respect to the actuator 124 and the force applicator 126 may extend between the two stabilizers 122 and the actuator 124. As depicted in FIG. 5, the stabilizers 122 may be spaced an equal distance or substantially equal distance from the actuator 124. Such a configuration of the stabilizers 122 with respect to the actuator 124 may facilitate applying a substantially equal force to the floor or other surface 561 supporting the cart 102 at each of the stabilizers 122. For example, the actuator 124 may be configured to pull down on the force applicator 126 (e.g., pull the force applicator 126 toward the floor or other surface 561) and cause the two stabilizers 122 to move from a resting or retracted position (e.g., the undeployed position) to a deployed position and apply equal or substantially equal force to the floor or other surface 561.

The stabilizers 122 may be coupled to the actuator 124 via the force applicator 126 such that the actuator 124 may act on the force applicator 126 to cause the force applicator 126 to apply a force to the stabilizers 122. The stabilizers 122 may be coupled to the force applicator 126 in any suitable manner. Example couplings between the force applicator 126 and the stabilizers 122 may include, but are not limited to, a pin connection, a locking pin connection, a threaded connection, a luer lock connection, a bayonet connection, a friction fit connection, a snap connection, or other suitable couplings.

The stabilizers 122 and the actuator 124 may be coupled to the force applicator 126 at any suitable location. In one example, the first stabilizer 122a may be coupled to or interact with a first end of the force applicator 126, the second stabilizer 122b may be coupled to or interact with a second end of the force applicator 126, and the actuator 124 may be coupled to or interact with a portion of the force applicator 126 between the first end and the second end, but other configurations are contemplated.

In one example configuration of the coupling between the force applicator 126 and the stabilizers 122, as depicted in FIG. 5, the stabilizers 122 may be coupled to the force applicator 126 with a connector 562 (e.g., a clip, a retaining clip, a pin, a screw, a bolt, a nut, bracket, etc., which may be a component of the stabilizers 122) extending around a portion of the stabilizers 122. In the example, a portion of a biaser housing 568 of the stabilizer 122 may be inserted into the force applicator 126 and the connector 562 may be applied through, around, or otherwise connected to the portion of the biaser housing 568 inserted into the force applicator 126 to couple the stabilizer 122 with the force applicator 126. In such a configuration, when the actuator 124 is adjusted or otherwise actuated, the force applicator 126 may act on an outer surface of the stabilizers 122 to cause the stabilizer to move between retracted and deployed positions.

The stabilizers 122 may have any suitable configuration. In some cases, the stabilizers 122 may be configured to apply a predetermined amount of force to the floor or surface 561 in response to the actuator 124 acting thereon. Although not required, a predetermined amount of force applied to the floor or surface 561 may be an amount of force applied to the floor or surface 561 when the stabilizer 122 is in the deployed that is less than an amount of force required to lift the cart 102 off of the floor, but provides enough force on the floor or surface 561 to stabilize the cart 102 and resist, prevent, or substantially prevent the cart 102 from moving when the stabilizers 122 are in the deployed position.

Although other force amounts are contemplated and may depend on a mass or other configuration of the cart 102, an example predetermined amount of force applied to the surface or floor 561 when the stabilizers 122 are in the deployed position without lifting the cart 102 may be a force amount in a range of eighty or about eighty pounds of force to one-hundred or about one-hundred pounds of force. Other suitable amounts of force are contemplated.

In one example configuration, as depicted in FIG. 5, the stabilizers 122 may include one or more feet 123 configured to contact the floor or other surface 561 to support the surgical cart 102 when the stabilizers 122 are in the deployed position, the rod 564 that may be in communication with the feet 123, a support or plate 574 that may be fixed to or fixed relative to the rod 564 and may translate with the rod 564 (e.g., the support or plate 574 and the rod may axially adjust within a biaser housing 568) and the foot 123, and a biaser 566. In some cases, the biaser 566 may be configured to bias the foot 123 in a retracted position and contribute to a predetermined amount of force applied to the floor or surface 561 supporting the cart 102 when the foot 123 is in a deployed position. Alternatively, the biaser 566 may be configured to bias the foot 123 in the deployed position.

The feet 123 may take on any suitable configuration. In some cases, the feet 123 may have a rounded, a squared, a circular, or other suitable configuration for supporting and stabilizing the cart 102 when the stabilizers 122 are in the deployed configuration. The feet 123 can be constructed from any of a variety of materials. In an example, the feet 123 are constructed from plastic.

The foot 123 may be coupled to or otherwise connected to the rod 564 in any suitable manner. In one example, the foot 123 may be rigidly coupled to the rod 564 such that the foot 123 cannot move independent of the rod 564. In another example, the foot 123 may be pivotally or otherwise adjustably coupled to the rod 564. When pivotally or otherwise adjustably coupled to the rod 564, the foot 123 may be configured to facilitate stabilizing the cart on an uneven floor or surface.

The rods 564 may take on any suitable configuration. As depicted in FIG. 5, the rods 564 may have a first portion 564a and a second portion 564b, but this is not required and the rod 564 may have a single portion or more than two portions. When one or more of the rods 564 have more than one portions, the rods 564 may be connected in any suitable manner including, but not limited to, weld connections, threaded connections, adhesive connections, over molding connections, etc.

The support or plate 574 may take on any suitable configuration. In one example, the support or plate 574 be configured to translate within the biaser housing 568, further discussed below, and may extend around the rod 564 such that the plate 574 may support an end of a second spring (e.g., a second spring 572, further discussed below) of the biaser 566.

Further, in some cases, the stabilizers 122 may include one or more supports 576 extending toward the floor or other surface 561 from the base 130 of the cart 102 and the rods 564 may extend through the one or more supports 576. The supports 576, when included, may facilitate structurally supporting the feet 123 adjacent the support 576 or the rods 564 extending through the supports.

The supports 576 may include adjustable bearings 580 (e.g., bearings made of metal, rubber, etc.) that may extend from the supports 576 to support the feet 123. Any suitable number of bearings may be utilized. For example, a single bearing may be utilized, two bearings may be utilized, three bearings may be utilized, ten bearings may be utilized, etc. Further the bearings 580 may take on any suitable shape configured to support or otherwise contact the feet 123 when the feet 123 are in the resting or retracted position (e.g., a non-stabilizing position). Example shapes include, but are not limited to, full-circle shapes, half-circle shapes, ornamental shapes, ring shapes, dot shapes, etc. As depicted in the Figures, three bearings are utilized and each bearing has a rounded dot configuration with an elongated threaded portion for coupling to the support 576. Other configurations are contemplated for coupling the bearings 580 to the supports 576. Additionally or alternatively to the bearings 580 being of or otherwise coupled to the supports 576, the bearings may be of or coupled to the feet 123.

The biaser 566 may include one or more components configured to bias the foot 123 and the stabilizer 122 in the retracted position and contribute to a predetermined amount of force applied to the floor or surface 561 supporting the cart 102 when the foot 123 and the stabilizer 122 are in the deployed position. Among other components, the biaser 566 may include the biaser housing 568, a first spring 570 biasing the stabilizer 122 to a retracted or resting position, and a second spring 572 biasing the stabilizer 122 to a deployed position, as depicted in FIG. 5.

The biaser housing 568 may take on any suitable configuration. In some cases, the biaser housing 568 may have a first portion 568a and a second portion 568b. As depicted in FIG. 5, first portion 568a of the housing 568 may be configured to be received within the second portion 568b of the housing 568. The first portion 568a and the second portion 568b of the biaser housing 568 may be fixed with respect to one another. Alternatively, the first portion 568a and the second portion 568b may be configured to slide or otherwise adjust with respect to one another in response to external, internal, or both external and internal forces acting on the stabilizer 122. Other configurations of the housing 568 are contemplated.

The first spring 570 of the biaser 566 may be located at any suitable location with respect to the biaser housing 568. In one example, the first spring 570 of the biaser 566 may be entirely or at least partially exterior of the biaser housing 568 (e.g., the first spring 570 may extend along an exterior of the biaser housing 568) and configured to bias the stabilizer 122 to a retracted position by acting on the biaser housing 568 in a direction of arrow D2 (e.g., away from the surface 561 in a direction substantially perpendicular to the surface 561). Although not required, the first spring 570 may extend between a surface of the base 130 of the cart 102 and the second portion 568b of the housing 568. In such a configuration, the first spring 570 may act on the base 130 and the biaser housing 568 to bias the stabilizer 122 to the retracted or resting position.

The second spring 572 of the biaser 566 may be located at any suitable location with respect to the biaser housing 568. In one example, the second spring 572 of the biaser 566 may be entirely or at least partially within an interior of the biaser housing 568 (e.g., the second spring 572 may extend along an interior of the biaser housing 568) and configured to bias the stabilizer 122 to a deployed position by acting on the support or plate 574 in a direction of arrow D1 (e.g., toward from the surface 561 in a direction substantially perpendicular to the surface 561). Although not required, the second spring 572 may extend between the second portion 568b (e.g., an interior surface of the second portion 568b) of the biaser housing 568 and the first portion 568a of the biaser housing 568 or the plate 574 extending around the rod 564 within the biaser housing 568. In a configuration where the second spring 572 extends between the second portion 568b of the biaser housing 568 and the support or plate 574, the second spring 572 may act on the biaser housing 568 and the support or plate 574 to contribute to a predetermined amount of force applied to the floor or other surface 561 stabilizing the cart 102 when the stabilizer 122 is in the deployed position.

The first spring 570 and second spring 572 may have any suitable shape or configuration. In one example, the second spring 572 may have a smaller diameter than the first spring 570, the second spring 572 have a longer relaxed state than the first spring 570, and the first spring 570 and the second spring 572 may have one or more other similar or different configurations, but this is not required.

The first and second springs 570, 572 may each have any suitable spring constant. The spring constants may be determined, selected, or set based on one or more of a variety of factors, including, but not limited to, a mass of equipment on the cart 102, a mass of the cart 102, desired relative spring constants between the first spring 570 and the second spring 572, an amount of force the actuator 124 may be able to overcome, a desired amount of force to be applied to the floor or surface 561 by the stabilizers 122, etc. In one example, a spring constant of the first spring 570 may be less than a spring constant of the second spring 572 such that the first spring 570 contributes to an amount of force needed (e.g., an amount of force the actuator 124 applies to the force applicator 126) to advance the stabilizer 122 from the retracted position to a position at which the stabilizer 122 contacts the floor or surface 561. The spring constant of the second spring 572 may be greater than a spring constant of the first spring 570 such that the spring constant of the second spring 572 may contribute to an amount of force applied to the floor or surface 561 by the stabilizer 122 in a deployed configuration after the stabilizer 122 contacts the floor or surface 561.

As depicted in FIG. 5, when the stabilizers 122 are in a retracted or resting position, the first springs 570 are expanded between the base 130 and second portion 568b of the biaser housing 568 and have a length S1. In the retracted or resting position of the stabilizers 122, the second springs 572 extend between the second portion 568b of the biaser housing 568 and the plate 574 and have a length S2. The actuator 124 has a length of S3 when the stabilizers 122 are in the retracted or resting position.

The stabilizers 122 may transition from the retracted or resting position to a deployed position in response to actuation of the actuator 124, as discussed below with respect to FIGS. 6 and 7. Other suitable configurations are contemplated for transitioning between the retracted or resting position and the deployed positions.

Figure 6:
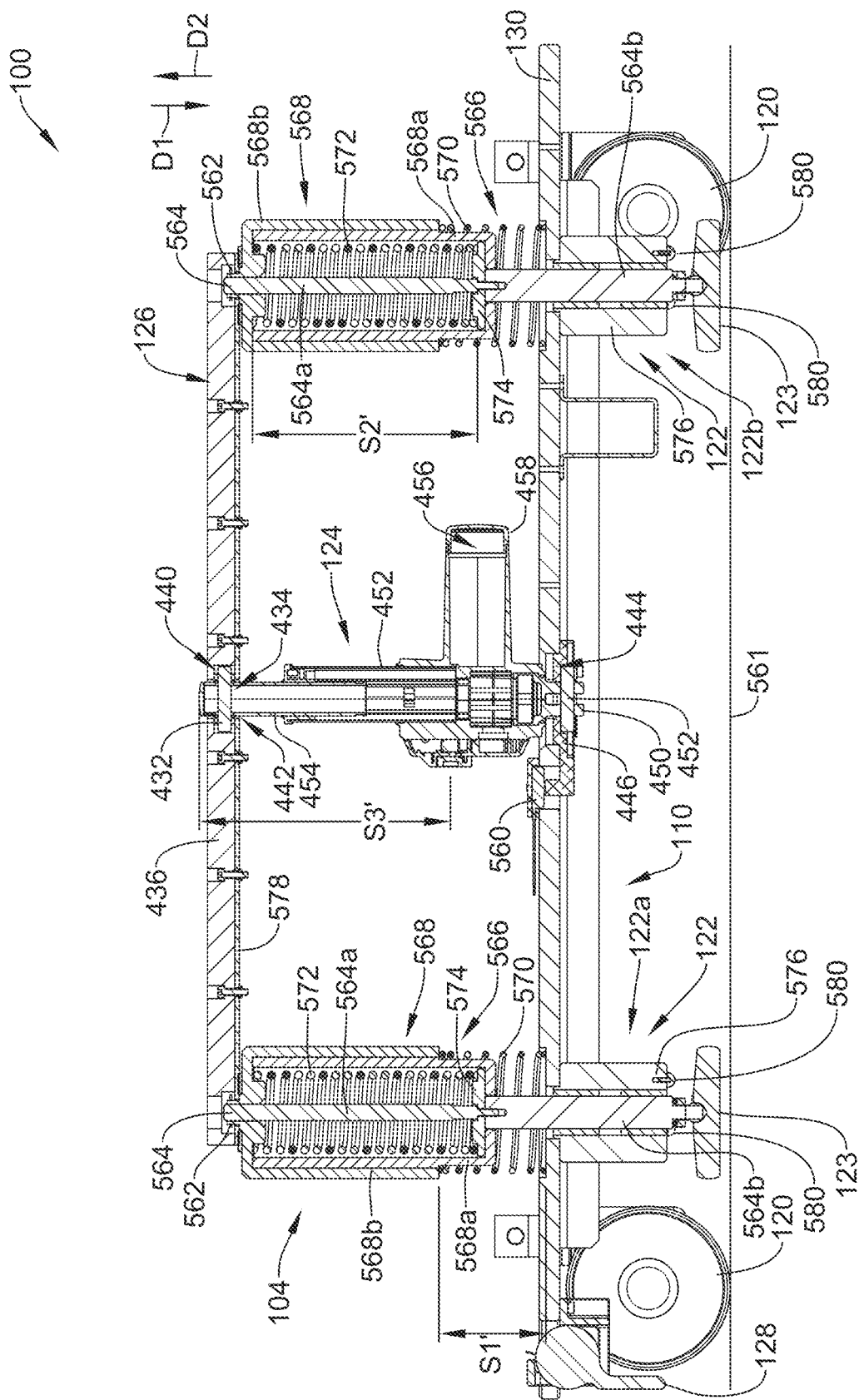
FIG. 6 the schematic cross-sectional view of FIG. 5, in which an actuator is partially actuated.
Figure 7:
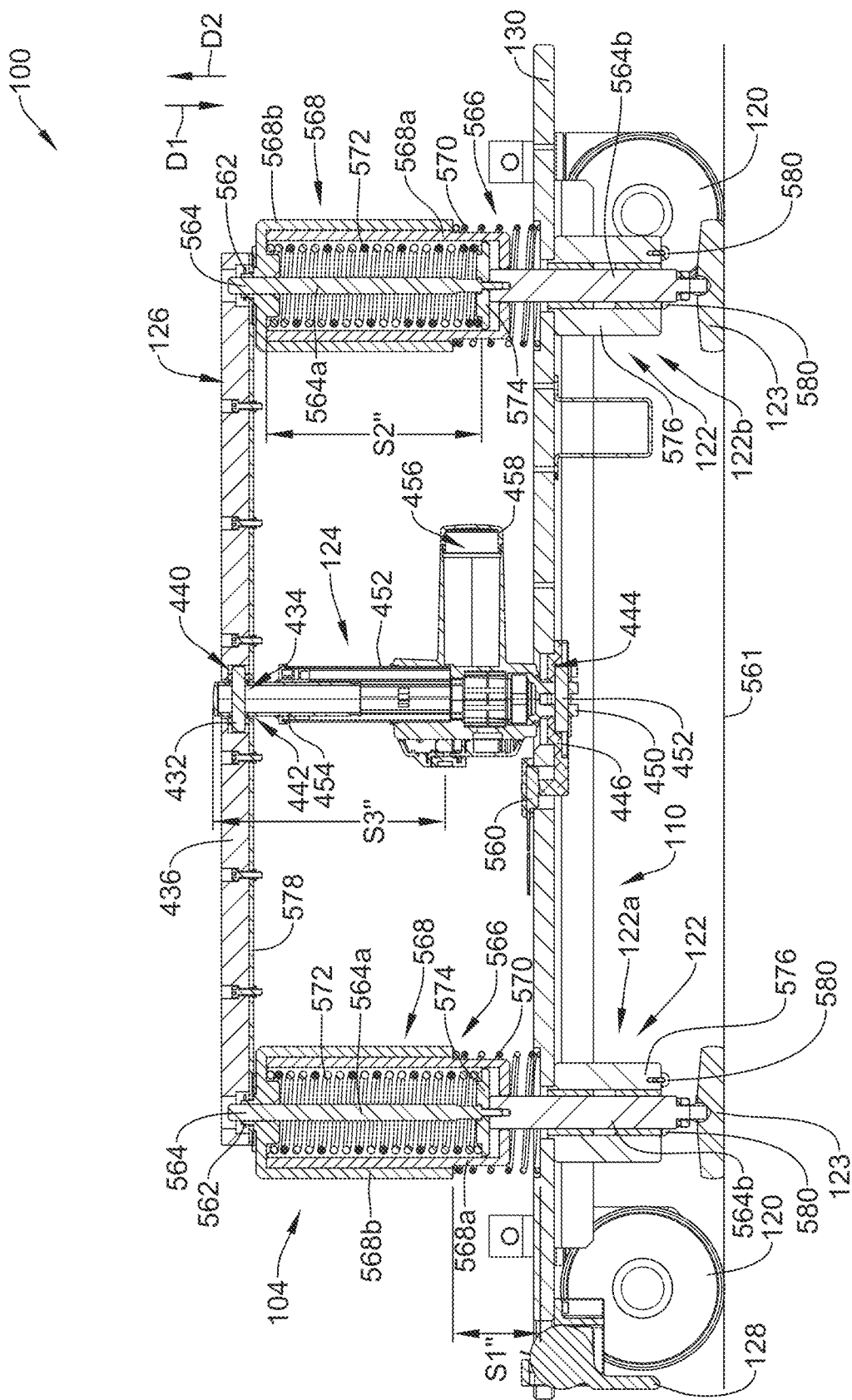
FIG. 7 the schematic cross-sectional view of FIG. 5, in which the actuator is fully actuated.

FIGS. 6 and 7 depict the transition of the stabilizers 122 of the cart from a retracted or resting position (e.g., as depicted in FIG. 5) to a fully deployed position (e.g., as depicted in FIG. 7). The stabilizers 122 transition from the retracted or resting position to the fully deployed position in response to adjustment of the actuator 124, but other configurations are contemplated.

The cross-sectional view of the cart assembly 100 in FIG. 6 depicts, among other features, the stabilizers 122 in a transitional position between the retracted or resting position and the fully deployed position at which the actuator 124 has been adjusted from a length of S3 (as in FIG. 5) to a length of S3' that is shorter than the length S3. In adjusting the actuator 124, the actuator 124 pulls down on the force applicator 126 and the stabilizers 122 toward the floor or other surface 561 in a direction of arrow D1. As the stabilizers 122 are moving from the retracted position to the deployed position, each foot 123 of the stabilizers 122 may initially translate with the force applicator 126 and the biaser housing 568. That is, in adjusting to the transitional position, the actuator 124 at least partially overcomes the bias force of the first spring 570 and causes the first spring 570 to have a reduced length S1' that is shorter than the length S1. At this point, the second spring 572 has a length of S2' that is equal to or substantially equal to the length S2, and the feet 123 are at a partially deployed state at which the feet 123 are spaced from the floor or other surface 561.

The cross-sectional view of the cart assembly 100 in FIG. 7 depicts, among other features, the stabilizers 122 in the fully deployed position at which the actuator 124 has been adjusted to a desired position, such that a length of the actuator 124 has changed from a length of S3 (as in FIG. 5) to a length of S3" that is shorter than the lengths S3 and S3'. In some cases, the position of the actuator 124 in the fully deployed position may be a predetermined linear location that is configured, in conjunction with a configuration of the stabilizers, to cause a known amount of force to be applied to the floor or other surface 561. Such deployment can be without respect to a force sensor or other sensor and can simplify the system. Alternatively or additionally, the position of the actuator 124 may be determined in response to measured or sensed values of force applied to the floor or other surface 561 by the feet 123 as the actuator 124 is adjusted. For example, the actuator 124 may be adjusted until a desired (e.g., predetermined or otherwise) amount of force is applied to the floor or other surface 561 by the feet 123, but this is not required. Driving the actuator 124 to a predetermined linear location to cause a known amount of force to be applied to the floor or other surface 561 may simplify a control of the stabilizer system 104 over other stabilizing systems that may utilize a controller to adjust an actuator until a desired stabilizing force is applied to a supporting surface.

In adjusting to the fully-deployed position, the actuator 124 may overcome the bias force of the first spring 570 and when at the predetermined linear location, cause the first spring 570 to have a further reduced length S1" that is shorter than the length S1 and S1' and at which the foot 123 of the stabilizer 122 contacts the floor or other surface 561. Once the foot 123 of the stabilizer 122 contacts the floor or other surface 561, the foot 123 or one or more of the components indirectly or directly coupled to the foot 123, such as the rod 564, the support or plate 574, the second spring 572, or a combination thereof, may adjust (e.g., translate) relative to the force applicator 126 and the biaser housing 568, as depicted in FIG. 7, until the actuator 124 is at the predetermined linear position and the predetermined amount of force is applied to the floor or other surface 561 by the foot 123. In an example, the rod 564, the support plate 574, and the second spring 572 may adjust relative to the force applicator 126 and the biaser housing 568 until the predetermined amount of force is applied to the floor other surface 561. That is, once the feet 123 are contacting the floor or other surface 561 and the actuator 124 is at the predetermined linear position, the second spring 572 may compress to a length of S2" that is shorter than the lengths S2 and S2' and at which the feet 123 are in contact with and applying a desired amount of force to the floor or other surface 561 to stabilize the cart 102 at a desired location.

In some cases, the desired or predetermined amount of force applied to the floor or surface 561 may be entirely or at least partially dependent on the spring constant of the second spring 572. In one example, the predetermined amount of force applied to the floor or surface 561 may be dependent on the spring constant of the second spring and a distance the actuator 124 travels after the feet 123 contact the floor or surface 561, but this is not required.

As discussed, the actuator 124 may be adjusted to move the stabilizers 122 between the retracted or resting position and the deployed position. In some cases, the actuator 124 may be configured to adjust between a first predetermined position associated with the resting or retracted position (e.g., the undeployed position) and a second predetermined position associated with the deployed position of the stabilizers 122. The second predetermined position of the actuator 124 that is associated with the deployed position of the stabilizers 122 may be a location independent of or irrespective of an amount of force the feet 123 of the stabilizers 122 apply to the floor or other surface 561 in the deployed position. For example, the second predetermined position of the actuator 124 may be set to cause the feet 123 of the stabilizers 122 to contact the floor or surface 561 and once the feet 123 are in contact with the floor or surface 561, the force caused by the spring constant of the second spring 572 may cause the feet 123 to apply the predetermined amount of force to floor or other surface 561. That is, the actuator 124 may drive the stabilizer 122 between the retracted position and the deployed position without regard to an amount of force being applied to the floor by the stabilizer 122. Such a configuration of the actuator 124 relative to the stabilizer 122 may allow for a simplified control of the actuator 124 and the stabilizer 122 due to only needing to adjust the actuator 124 to a single, known or predetermined position each time the stabilizer 122 is to be deployed.

Figure 8:
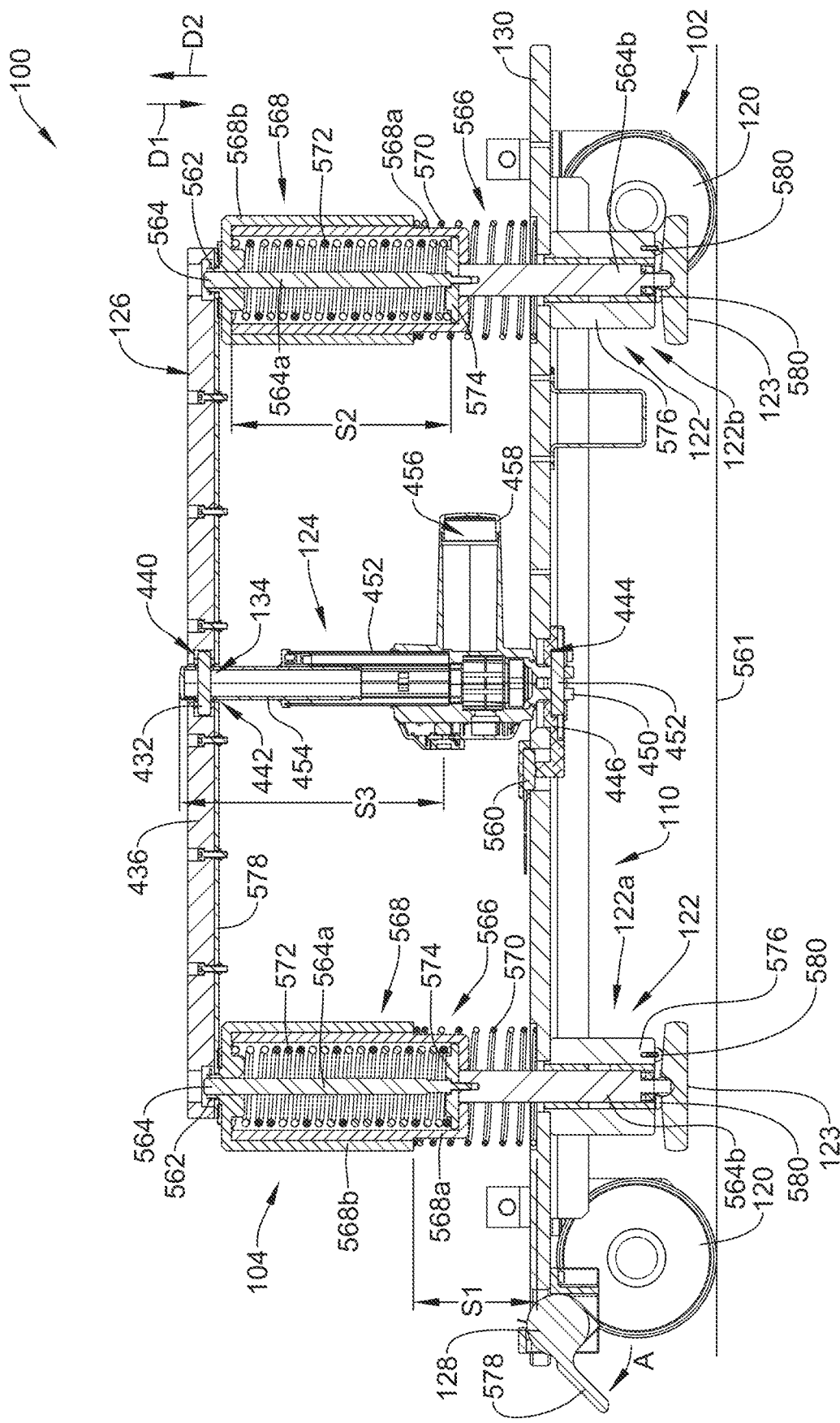
FIG. 8 the schematic cross-sectional view of FIG. 5, in which an emergency release is actuated.

The actuator 124 may be adjusted manually (e.g., in response to adjustment of a lever or other mechanical mechanism) or in an automated manner in response to a control signal manually initiated by a user selection or automatically initiated. In some cases, however, it may be desirable to quickly release the stabilizers from the deployed position (e.g., to facilitate moving the cart away from a surgical site in response to an emergency or for one or more other suitable purposes). To facilitate a quick or emergency release of the stabilizers 122, the emergency release 128 may be actuated. In one example, the emergency release 128 may be a mechanical release that is actuated from a first position with the stabilizers 122 in the fully-deployed position (e.g., as depicted in FIG. 7) to a second position (e.g., as depicted in FIG. 8) that causes or otherwise results in the stabilizers 122 being retracted in the second direction of arrow D2 to the retracted position. In the configuration depicted in FIG. 8, the emergency release 128 may be rotated in the direction of arrow A, however, other configurations of the emergency release are contemplated including, but not limited, to a push button.

The emergency release 128 may be adjusted manually (e.g., in response to adjustment of a lever or other mechanical mechanism), may be adjusted in an automated manner in response to a control signal automatically initiated or manually initiated by a user selection, or may be configured to be adjusted manually or in an automated manner. When con figured to be adjusted manually, the emergency release 128 may be include a grip portion 578 that may be engaged by a user's hand or foot or other suitable component to facilitate actuating the emergency release 128.

The emergency release 128 may be connected or coupled to the actuator 124 or other component of the stabilizers 122 that may facilitate moving the stabilizers 122 to a retracted position in any suitable manner. In one example, the emergency release 128 may be mechanically, electrically, or both mechanically and electrically connected or coupled to actuator 124 such that actuation of the emergency release 128 causes the actuator 124 or other suitable component of the stabilizer system 104 to mechanically release from an actuated position at which the actuator 124 has the length S3" to a relaxed position, causing the stabilizer(s) 122 to automatically move from the deployed position at which the first spring has the length S1" and the second spring has the length S2" to the retracted position, as depicted in FIG. 8, such that the first spring 570 has the length S1, the second spring 572 has the length S2, and the actuator has the length S3.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the term "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The above detailed description should be read with reference to the drawings in which similar elements in different drawings are numbered similarly. The drawings, which are not necessarily to scale, depict illustrative embodiments and are not intended to limit the scope of the invention.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

The invention claimed is:

1. An assembly comprising:
   a surgical cart having locking caster wheels configured to contact a floor;
   a stabilizer comprising:
      a foot configured to resist movement of the surgical cart when the foot is in a deployed position contacting the floor; and
      a biaser configured to bias the foot in a retracted position and contribute to a predetermined amount of force applied to the floor when the foot is in the deployed position, the biaser comprising a biaser housing and a spring extending within the biaser housing;
a rod;
a plate fixed relative to the rod; and
an actuator configured to drive the stabilizer toward the deployed position; and
wherein the foot is connected to the rod,
wherein actuation of the actuator causes the stabilizer to:
adjust to the deployed position and apply the predetermined amount of force to the floor, and wherein the spring is configured to act on the biaser housing and the plate to contribute to the predetermined amount of force applied to the floor when the stabilizer is in the deployed position
wherein the biaser comprises:
a first spring biasing the stabilizer to the retracted position; and
a second spring biasing the stabilizer to the deployed position;
wherein the biaser comprises:
a housing, wherein the first spring extends along an exterior of the housing and the second spring extends along an interior of the housing.

2. The assembly of claim 1, wherein:
the surgical cart comprises a surgical cart base; and
the biaser comprises:
a biaser housing; and
a spring configured to act on the surgical cart base and the biaser housing to bias the stabilizer in the retracted position.

3. The assembly of claim 1, further comprising:
a force sensor configured to directly or indirectly measure an amount of force applied to the floor when the stabilizer is in the deployed position.

4. The assembly of claim 1, wherein the predetermined amount of force applied to the floor when the stabilizer is in the deployed position is less than a force required to lift the surgical cart off of the floor.

5. The assembly of claim 1, wherein the predetermined amount of force applied to the floor when the stabilizer is in the deployed position is within a range of 80 pounds of force to 100 pounds of force.

6. The assembly of claim 1, further comprising:
wherein the stabilizer is a first stabilizer;
wherein the assembly further comprises a second stabilizer spaced from the first stabilizer; and
wherein the actuator is configured to simultaneously drive the first stabilizer and the second stabilizer toward the deployed position.

7. The assembly of claim 1, further comprising:
a mechanical release, wherein the mechanical release is configured to mechanically disengage the actuator and cause the stabilizer to move from the deployed position to the retracted position.

8. The assembly of claim 1, wherein the actuator is configured to drive the stabilizer between the retracted position and the deployed position.

9. A system comprising:
a first stabilizer and a second stabilizer for stabilizing a surgical cart on wheels, wherein each of the first and second stabilizers comprise a foot configured to contact a floor to support the surgical cart when the stabilizer is in the deployed position and a biaser configured to bias the stabilizer in the retracted position and contribute to an amount of force the foot applies to the floor in the deployed position;
a force applicator extending between the first stabilizer and the second stabilizer; and
a linear actuator configured to pull down on the force applicator to cause the first and second stabilizers to move from a retracted position to a deployed position,
wherein the foot of each stabilizer is configured to initially translate with the force applicator and a biaser housing of the biaser when the stabilizer is moving from the retracted position to the deployed position and once the foot of each stabilizer contacts the floor, translate relative to the force applicator and the biaser housing,
a force sensor in communication with the linear actuator, the force sensor is configured to sense a force indicative of a force the first stabilizer and the second stabilizer apply to a floor contacting the first stabilizer and the second stabilizer when the first stabilizer and the second stabilizer are in the deployed position; and
a controller configured to classify the deployment of the first stabilizer and the second stabilizer as being successful or unsuccessful based on an amount of force detected by the force sensor.

10. The system of claim 9, wherein the force applicator includes:
a first end interacting with the first stabilizer;
a second end interacting with the second stabilizer; and
a portion between the first end and the second end that is coupled to the linear actuator.

11. The system of claim 10, further comprising:
wherein the force applicator extends between the linear actuator, the first stabilizer, and the second stabilizer; and
wherein the linear actuator is arranged to pull the force applicator toward a floor supporting the surgical cart to cause the first and second stabilizers to move toward the deployed position.

12. The system of claim 9, wherein the linear actuator is configured to adjust between a first predetermined position associated with the retracted position and a second predetermined position associated with the deployed position irrespective of the amount of force the feet of the first and second stabilizers apply to the floor in the deployed position.

* * * * *